US012668831B2

(12) United States Patent
Lesner et al.

(10) Patent No.: US 12,668,831 B2
(45) Date of Patent: Jun. 30, 2026

(54) DIAGNOSTIC MARKER FOR PANCREATIC CANCER

(71) Applicant: URTESTE S.A., Gdansk (PL)

(72) Inventors: Adam Lesner, Gdansk (PL); Natalia Gruba, Keblowo (PL)

(73) Assignee: URTESTE S.A., Gdansk (PL)

( * ) Notice: Subject to any disclaimer, the term of this patent is extended or adjusted under 35 U.S.C. 154(b) by 581 days.

(21) Appl. No.: 17/622,070

(22) PCT Filed: Jun. 23, 2020

(86) PCT No.: PCT/EP2020/067542
§ 371 (c)(1),
(2) Date: Dec. 22, 2021

(87) PCT Pub. No.: WO2020/260309
PCT Pub. Date: Dec. 30, 2020

(65) Prior Publication Data

US 2022/0251625 A1 Aug. 11, 2022

(30) Foreign Application Priority Data

Jun. 24, 2019 (PL) .................................. 430348
Jan. 2, 2020 (EP) .................................. 20150093
Mar. 27, 2020 (EP) .................................. 20166354

(51) Int. Cl.
*C12Q 1/37* (2006.01)
*G01N 33/58* (2006.01)

(52) U.S. Cl.
CPC ............ *C12Q 1/37* (2013.01); *G01N 33/582* (2013.01); *G01N 2800/06* (2013.01)

(58) Field of Classification Search
CPC ..... C12Q 1/37; G01N 22/582; G01N 2800/06
See application file for complete search history.

(56) References Cited

U.S. PATENT DOCUMENTS

2004/0180395 A1 9/2004 Richard et al.
2011/0014125 A1* 1/2011 Bossmann ......... A61K 49/0036 977/773
2012/0107858 A1 5/2012 Yoo et al.
2016/0033511 A1 2/2016 Pannell et al.
2016/0168618 A1 6/2016 Kim et al.
2017/0096699 A1 4/2017 Asakura et al.
2019/0195852 A1 6/2019 Bryant, Jr. et al.
2020/0385469 A1* 12/2020 Yang ................. C07K 16/2809

FOREIGN PATENT DOCUMENTS

CA 2 425 829 A1 5/2002
CN 1514878 A 7/2004
CN 101685080 A 3/2010
EP 2 275 809 A1 1/2011
EP 2 851 688 A1 3/2015
EP 3431490 1/2019
KR 102009005223 A 5/2009
PL 408905 A1 1/2016
PL 225341 B1 3/2017
PL 422233 A1 1/2019
PL 236125 B1 12/2020
PL 238575 B1 9/2021
PL 238699 B1 9/2021
WO WO 2002/038744 A2 5/2002
WO WO 2012/118715 A2 9/2012
WO WO 2018/187385 A1 10/2018
WO WO 2023/180181 A1 9/2023

OTHER PUBLICATIONS

Nitsche, Christoph, et al. "Biochemistry and medicinal chemistry of the dengue virus protease." Chemical reviews 114.22 (2014): 11348-11381. (Year: 2014).*
PCT International Patent Application Publication No. WO 2004/099432 A2, (The Johns Hopkins University [US/US] ) , published Nov. 18, 2004.
PCT International Patent Application Publication No. WO 2004/102189 A1, (Europroteome AG [DE/DE] ) , published Nov. 25, 2004.
PCT International Patent Application Publication No. WO 2011/101330 A1, (Deutsches Krebsforschungszentrum [DE/DE] ), published Aug. 25, 2011.
PCT International Patent Application Publication No. WO 2014/108480 A1, (Friedrich-Alexander-Universitaet Erlangen-Nuernberg [DE] ) , published Jul. 17, 2014.

(Continued)

*Primary Examiner* — Robert J Yamasaki
*Assistant Examiner* — Trevor Kane
(74) *Attorney, Agent, or Firm* — Gary J. Gershik

(57) ABSTRACT

The invention provides a compound characterized by formula (1): X1-Thr-Thr-Ala-Arg-X2, wherein cleavage of the compound into a fragment 1 comprising X1 and a fragment 2 comprising X2 generates a detectable signal. The invention further provides an in vitro method for detecting protease activity in a subject's body fluid, comprising contacting the body fluid with the compound of the invention and detecting a signal, wherein the body fluid may comprise a hydrolytic enzyme derived from pancreatic cancer cells. Furthermore, the invention provides a kit comprising the compound of the invention and a measurement buffer. In addition, the invention provides the use of the compound, the in vitro method or the kit of the invention for the detection of pancreatic cancer, or for monitoring a subject that is suspected of having pancreatic cancer, has an increased risk of developing pancreatic cancer, or has had pancreatic cancer. The invention also provides the use of the compound of the invention in a method of treating pancreatic cancer, the method comprising carrying out the in vitro method for detecting protease activity in a subject's body fluid, and treating pancreatic cancer in a subject for which protease activity, has been detected.

28 Claims, 3 Drawing Sheets

Specification includes a Sequence Listing.

(56) References Cited

OTHER PUBLICATIONS

PCT International Patent Application Publication No. WO 2017/137741 A1, (Mdb Medical Services Limited [GB/GB] ) , published Aug. 17, 2017.
PCT International Patent Application Publication No. WO 2017/152042 A2, (New York University [US/US]), published Sep. 8, 2017.
PCT International Patent Application Publication No. WO 2019/075292 A1, (Massachusetts Institute of Technology [US/US] ) , published Apr. 18, 2019.
PCT International Patent Application Publication No. WO 2019/126576 A1, (Amunix Pharmaceuticals, Inc. [US/US] ) , published Jun. 27, 2019.
Hasan, S. et al., "Advances in pancreatic cancer biomarkers," Oncology Reviews, 2019, vol. 13, pp. 69-76.
Radon, T.P. et al., "Identification of a three-biomarker panel in urine for early detection of pancreatic adenocarcinoma", Clin Cancer Res., 2015, vol. 21, pp. 3512-3521.
European Search Report issued by the European Patent Office on Jun. 9, 2020 in connection with European Application No. EP 20 15 0093.
Polish Search Report issued by the Polish Patent Office on Nov. 5, 2019 in connection with Polish Patent Application No. P. 430348.
Dec. 30, 2020 Written Opinion issued in connection with PCT International Application No. PCT/EP2020/067542.
U.S. Patent Application Publication No. 2012/0107858 A1, published May 3, 2012 (Yoo et al.).
U.S. Patent Application Publication No. 2016/0168618 A1, published Jun. 16, 2016 (Kim et al.).
U.S. Patent Application Publication No. 2019/0195852 A1, published Jun. 27, 2019 (Bryant, Jr. et al.).
PCT International Patent Application Publication No. WO 2004/099432 A2, (The Johns Hopkins University [US/US]), published Nov. 18, 2004 (Exhibit 1).
PCT International Patent Application Publication No. WO 2004/102189 A1, (Europroteome Ag [DE/DE]), published Nov. 25, 2004 (Exhibit 2).
PCT International Patent Application Publication No. WO 2011/101330 A1, (Deutsches Krebsforschungszentrum [ DE/DE]), published Aug. 25, 2011 (Exhibit 3).
PCT International Patent Application Publication No. WO 2014/108480 A1, (Friedrich-Alexander-Universitaet Erlangen-Nuernberg [DE]), published Jul. 17, 2014 (Exhibit 4).
PCT International Patent Application Publication No. WO 2017/137741 A1, (Mdb Medical Services Limited [GB/GB]), published Aug. 17, 2017 (Exhibit 5).
PCT International Patent Application Publication No. WO 2017/152042 A2, (New York University [US/US]), published Sep. 8, 2017 (Exhibit 6).
PCT International Patent Application Publication No. WO 2019/075292 A1, (Massachusetts Institute of Technology [US/US]), published Apr. 18, 2019 (Exhibit 7).
PCT International Patent Application Publication No. WO 2019/126576 A1, (Amunix Pharmaceuticals, Inc. [US/US ]), published Jun. 27, 2019 (Exhibit 8).
Canadian Patent Publication No. CA 2 425 829 A1, published May 16, 2002 (Incyte Genomics, Inc.) (Exhibit 9).
Chinese Patent Application No. CN 101685080 A, published Mar. 31, 2010 (Suzhou Yuntai Biological Pharmaceutical Co., LTD.) (Exhibit 10).
European Patent Application No. EP 2 275 809 A1, published Jan. 19, 2011 (Sumitomo Bakelite Company Limited) (Exhibit 11).
European Patent Application No. EP 2 851 688 A1, published Mar. 25, 2015 (Nitto Boseki Co., Ltd) (Exhibit 12).
Polish Patent No. PL 225341 B1, published Mar. 31, 2017 (Uniwersytet Gdański) (Exhibit 13).
Polish Patent No. PL 236125 B1, published Dec. 14, 2020 (Uniwersytet Gdański) (Exhibit 14).
Polish Patent No. PL 238575 B1, published Sep. 6, 2021 (Uniwersytet Gdański) (Exhibit 15).
Polish Patent No. PL 238699 B1, published Sep. 27, 2021 (Uniwersytet Gdański) (Exhibit 16).
Polish Patent Application No. PL 408905 A1, published Jan. 18, 2016 (Uniwersytet Gdański) (Exhibit 17).
Polish Patent Application No. PL 422233 A1, published Jan. 28, 2019 (Uniwersytet Gdański) (Exhibit 18).
Hasan, S. et al., "Advances in pancreatic cancer biomarkers," Oncology Reviews, 2019, vol. 13, pp. 69-76 (Exhibit 19).
Radon, T.P. et al., "Identification of a three-biomarker panel in urine for early detection of pancreatic adenocarcinoma", Clin Cancer Res., 2015, vol. 21, pp. 3512-3521 (Exhibit 20).
European Search Report issued by the European Patent Office on Jun. 9, 2020 in connection with European Application No. EP 20 15 0093 (Exhibit 21).
Polish Search Report issued by the Polish Patent Office on Nov. 5, 2019 in connection with Polish Patent Application No. P. 430348 (Exhibit 22).
Dec. 30, 2020 Written Opinion issued in connection with PCT International Application No. PCT/EP2020/067542 (Exhibit 23) .
Office Action, including machine generated english translation, issued Apr. 2, 2026 in connection with corresponding Brazilian Patent Application No. 112021026192-3.

* cited by examiner

A

B

SEQUENCE LISTING

```
<160> NUMBER OF SEQ ID NOS: 1

<210> SEQ ID NO 1
<211> LENGTH: 4
<212> TYPE: PRT
<213> ORGANISM: Homo sapiens

<400> SEQUENCE: 1

Thr Thr Ala Arg
1
```

DIAGNOSTIC MARKER FOR PANCREATIC CANCER

CROSS-REFERENCE TO RELATED APPLICATIONS

This application is a § 371 national stage of PCT International Application No. PCT/EP2020/067542, filed Jun. 23, 2020, claiming priority of European Patent Application Nos. 20166354.9, filed Mar. 27, 2020, EP20150093.1, filed Jan. 2, 2020 and claiming priority of Polish Patent Application No. P430348, filed Jun. 24, 2019, the contents of each of which are hereby incorporated by reference into the application.

REFERENCE TO A SEQUENCE LISTING

This application incorporates-by-reference nucleotide and/or amino acid sequences which are present in the file named "211222 91829 97306 0013 Sequence Listing SC.txt", which is 1 kilobytes in size, and which was created Dec. 22, 2021 in the IBM-PC machine format, having an operating system compatibility with MS-Windows, which is contained in the text file filed Dec. 22, 2021 as part of this application.

The present invention relates to chemical compounds for use in the diagnosis of pancreatic cancer. In particular, the present invention relates to chromogenic peptides suitable for the detection of proteolytic enzymes within a sample.

BACKGROUND OF THE INVENTION

Pancreatic cancer often has a very poor prognosis, as it is usually diagnosed at a late stage. Due to the dynamics of this cancer, a five-year survival is rare. Approximately 250,000 cases of pancreatic cancer per year are diagnosed worldwide, and 3,500 in Poland. Unfortunately, the vast majority of cases ends in death (over 80%). There is an unmet need for reliable, fast and uncomplicated diagnostic methods for the detection of pancreatic cancer. Earlier diagnosis would enhance the chances for surgical treatment, which could significantly extend the patient's survival.

The process of initiation, growth and dissemination of cancer cells involves many factors including a number of proteolytic enzymes. This group of proteins is able to hydrolyze proteins and peptides into smaller fragments. Proteolytic enzymes mediate degradation of the extracellular matrix, thus allowing cancer cells to colonize new tissues, and enable the formation of new blood vessels (angiogenesis), which promotes efficient delivery of nutrients to the tumour. In addition, proteolytic enzymes are present as a result of the death of healthy cells due to the tumour growth process. All these processes form a profile of proteolytic enzymes that is characteristic for a tumour.

Chromogenic peptide molecules that break down under the influence of proteolytic enzymes, causing a change or increase in the colour of the solution being tested, have been described previously. This chromogenic effect is a consequence of the release of a chromophore (e.g. 4-nitroanilide or 5-amino-2-nitrobenzoic acid).

This type of peptide derivative is known from the following publications:

1. Erlanger B F, Kokowsky N, Cohen W. The preparation and properties of two new chromogenic substrates of trypsin. Arch Biochem Biophys. 1961 November; 95:271-8.

2. Hojo K, Maeda M, Iguchi S, Smith T, Okamoto H, Kawasaki K. Amino acids and peptides. XXXV. Facile preparation of p-nitroanilide analogs by the solid-phase method. Chem Pharm Bull (Tokyo). 2000 November; 48 (11): 1740-4.

Methods for detecting and measuring the expression of proteases have been described previously. The disclosed methods are based on isolated antibodies which specifically bind to specific polypeptides and PCR of the polynucleotides encoding the specific polypeptides. Demonstration of protease activity is measured by the hydrolysis of appropriate synthetic peptide substrates conjugated with chromogenic molecules, wherein the protease cleaves said synthetic substrate and the absorbance of the chromogen released during hydrolysis of the substrate is measured. (CA 2 425 829).

Preferred compounds according to the invention were developed in such a way that a signal, e.g. an increase in colour in the range of 380-440 nm, can be detected, if the compound is contacted with a urine sample of a person with pancreatic cancer. This effect does not occur if the compound is contacted with a urine sample of a healthy person or a patient diagnosed with another type of cancer.

The present inventors have discovered that such a signal, e.g. from a released chromogenic compound or a fluorescent signal after separation of a fluorescent donor/acceptor pair can be used to detect the presence of proteolytic enzymes in the urine of a subject having pancreatic cancer. Enzymatic hydrolysis of the compounds leads to the generation of a detectable difference, e.g. the release of free chromophore molecules (ANB-$NH_2$-amide of 5-amino-2-nitrobenzoic acid or pNA-para-nitroaniline, respectively), which show absorbance at 320-480 nm.

The compounds of the present invention provide inter alia: (i) a fast and non-invasive diagnostic method for the detection of pancreatic cancer, (ii) a method that is suitable for the early detection of pancreatic cancer, (iii) a method that can be successfully used for screening for pancreatic cancer, (iv) a full diagnostic process at an early stage of cancer development to introduce more effective treatment.

SUMMARY OF THE INVENTION

In a first aspect, the present invention relates to a compound characterized by formula 1:

X1-Thr-Thr-Ala-Arg-X2 (formula 1), wherein cleavage of the compound into a fragment 1 comprising X1 and a fragment 2 comprising X2 generates a detectable signal. The compound comprises the tetrapeptide Thr-Thr-Ala-Arg according to SEQ ID NO: 1.

In a second aspect, the present invention relates to an in vitro method for detecting protease activity in a subject's body fluid, comprising contacting the body fluid with the compound according to the first aspect of the invention and detecting a signal, wherein the body fluid may comprise a hydrolytic enzyme, in particular a protease, derived from pancreatic cancer cells.

In a third aspect, the present invention relates to a kit comprising the compound according to the first aspect of the invention and a measurement buffer.

In a fourth aspect, the present invention relates to use of the compound according to the first aspect of the invention, the method according to the second aspect of the invention or the kit according to the third aspect of the invention for the detection of pancreatic cancer, or for monitoring a subject that is suspected of having pancreatic cancer, has an increased risk of developing pancreatic cancer, or has had pancreatic cancer.

In a fifth aspect, the present invention relates to the use of the compound according to the first aspect of the invention in a method of treating pancreatic cancer, the method comprising the steps of (a) carrying out the method according to the second aspect of the invention, and (b) treating pancreatic cancer in a subject for which protease activity, in particular increased protease activity has been detected in step (a).

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art. Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

The terms and abbreviations used in the patent description and claims are to be understood as follows:

In the context of the invention a "detectable signal" refers to any signal such as generated by any label including a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles. The label can be e.g. chromophores, fluorophores, quantum dots, or radioactive labels.

In the context of the present invention, the expression "chromophore" is used to refer to a compound with "chromogenic properties". The expression "chromogenic properties" refers to the ability of a compound to form a coloured product.

In the context of the present invention, the expression "fluorophore" is used to refer to a compound with "fluorogenic properties". The expression "fluorogenic properties" refers to the ability of a compound to form a fluorescence emitting product.

Fluorescent dyes of the present invention comprise the following classes of dyes: Xanthens (e.g. Fluorescein), Acridines (e.g. Acridine Yellow), Oxazines (e.g. Oxazine 1), Cynines (e.g. Cy7/Cy 3), Styryl dyes (e.g. Dye-28), Coumarines (e.g. Alexa Fluor® 350), Porphines (e.g. Chlorophyll B), Metal-Ligand-Complexes (e.g. PtOEPK), Fluorescent proteins (e.g. APC, R-Phycoerythrin), Nanocrystals (e.g. Quantum Dot 705 (Qdot™ 705)), Perylenes (e.g. Lumogen® Red F 300) and Phtalocyanines (e.g. IRDYE™700DX) as well as conjugates and combinations of these classes of dyes.

A quantum dot is a semiconductor composed of atoms from groups II-VI or III-V elements of the periodic table (e.g., CdSe, CdTe, InP). Other alternatives include any two dyes system.

In the context of the present invention, NMP refers to N-methylpyrrolidone.

In the context of the present invention, DMF refers to dimethylformamide.

In the context of the present invention, DCM refers to methylene chloride.

In the context of the present invention, pNA refers to 4-nitroaniline, which may also be referred to as para-nitroaniline.

In the context of the present invention, ABZ refers to 2-aminobezenoic acid.

In the context of the present invention, ANB-NH2 refers to amide of 5-amino-2-nitrobenzoic acid.

In the context of the present invention, AFC refers to 7-amido-4-trifluoromethylcoumarin.

In the context of the present invention, Boc refers to tert-butyloxycarbonyl group.

In the context of the present invention, Fmoc refers to 9-fluorenylmethoxycarbonyl group.

In the context of the present invention, TFA refers to trifluoroacetic acid.

In the context of the present invention, the term "pancreatic cancer" is used in the broadest sense and refers to all cancers that start in the pancreas. It includes the subtypes exocrine cancers, endocrine cancers, pancreatoblastoma, sarcomas of the pancreas, and lymphoma. Exocrine cancers include adenocarcinomas, in particular ductal adenocarcinomas, as well as cystic tumours and cancer of the acinar cells. Endocrine cancers include gastrinomas, insulinomas, somatostatinomas, VIPomas, and glucagonomas. It also includes the following stages (as defined by the corresponding TNM classification(s) in brackets): stage 0 (Tis, N0, M0), stage IA (T1, N0, M0), stage IB (T2, N0, M0), stage IIA (T3, N0, M0), stage IIB (T1-3, N1, M0), stage III (T4, any N, M0), and stage IV (any T, any N, M1).

Peptides according to the present invention preferably chromogenic or fluorogenic peptides can be obtained by carrying out peptide synthesis on a solid support as known in the art. The solid support can be in the form of a resin having a Fmoc group, which is removed during the course of the reaction. The resin used to carry out this process should be properly prepared. The preparation of this resin comprises increasing its volume by repeated washing with hydrophobic solvents.

The Fmoc protecting group must be removed from the resin by washing with a 20% solvent solution.

Known processes of obtaining chromogenic peptides involve the attachment of individual components under appropriate time and stoichiometric conditions. This attachment process consists of subsequent stages, in which individual elements (amino acid derivatives) are attached, residues are washed off, and protecting groups are removed and washed again. This cycle is repeated for each amino acid residue. The resulting peptide is separated from the resin by reaction under acidic conditions. Subsequently, the solution is separated from the resin by filtration, and then the peptide is precipitated from the obtained solution with a non-polar solvent. The peptide sediment is then centrifuged.

The known method of obtaining chromogenic peptides is based on the process carried out on a solid support and partly in a buffer. An amide resin is used as a solid support, and a mixture of hydrophobic solvents is used as a solution.

The compounds according to the invention were prepared using the method described in Hojo et al., Chem Pharm Bull (Tokyo), 2000. A detailed description of the synthesis can be found below in the examples section.

Furthermore, the peptide according to the present invention may be linked to a quantum dot. Quantum dots are highly luminescent, except when quenched by the presence of a metal nanoparticle. Viologens (e.g. methylviologen or propyl viologen-sulfonate (PVS)) can also be used as quenchers.

Once the protease cleaves the consensus sequence, the quantum dot is released and lights up.

In a first aspect, the invention provides a compound characterized by formula 1: X1-Thr-Thr-Ala-Arg-X2 (formula 1), wherein cleavage of the compound into a fragment 1 comprising X1 and a fragment 2 comprising X2 generates a detectable signal.

In preferred embodiments, the sequence Thr-Thr-Ala-Arg is accessible for a hydrolytic enzyme, in particular a hydrolytic enzyme cleaving the compound into X1-Thr-Thr-Ala-Arg-OH (fragment 1) and $NH_2$-X2 (fragment 2).

The hydrolytic enzyme may be a protease or a combination of several proteases.

The detectable signal generated upon cleavage of the compound may be selected from various suitable signals known to the skilled person. In preferred embodiments, the detectable signal is an optical signal.

In preferred embodiments, X1 comprises or consists of a component C1 and X2 comprises or consists of a component C2, and the detectable signal is generated upon spatial separation of C1 and C2, i.e. by hydrolytic cleaving of the peptide Thr-Thr-Ala-Arg.

In addition to C1, X1 may e.g. comprise one or more amino acids on either side of C1. In addition to C2, X2 may e.g. comprise one or more amino acids on either side of C2. Thus, before cleavage, C1 and C2 may be separated by an amino acid sequence of 4 to 20 amino acids or 5 to 10 amino acids comprising or consisting of Thr-Thr-Ala-Arg. In preferred embodiments, C1 and C2 are separated by no more than 10 amino acids.

In preferred embodiments, the detectable signal is a change of absorption or fluorescence. Said change may be an increase or a decrease. In preferred embodiments, the detectable signal is an increase in absorbance intensity at 300-500 nm, in particular 380-430 nm.

In preferred embodiments, one of C1 and C2, is a chromophore having an absorption maximum 1 (AMI) at a wavelength 1, and the compound has an absorption maximum 2 (AM2) at a wavelength 2 that is different from wavelength 1. Thus, if absorption is measured at wavelength 2 before and after cleavage of the compound, an increase in absorption will be detected.

It is particularly preferred that upon cleavage, the chromophore is released in free form. Upon cleavage, fragment 1 consists of X1-Thr-Thr-Ala-Arg, while fragment 2 consists only of $NH_2$-X2. Thus, in preferred embodiments, the chromophore is C2 rather than C1. In instances where C2 is a chromophore, it is preferred that X2 consists of C2 or consists essentially of C2. X1 on the other hand may comprise additional amino acids on either side of C1, so that before cleavage, C1 and C2 may be separated by an amino acid sequence longer than Thr-Thr-Ala-Arg.

In preferred embodiments, the chromophore is selected from para-nitroaniline (pNA), amide of 5-amino-2-nitrobenzoic acid (ANB-$NH_2$), 7-amido-4-trifluoromethylcoumarin (AFC) and 3-nitro L-tyrosine (Tyr3-$NO_2$). In preferred embodiments, the chromophore is para-nitroaniline (pNA). In preferred embodiments, the chromophore is an amide of 5-amino-2-nitrobenzoic acid (ANB-$NH_2$).

In preferred embodiments, C1 and C2 are a pair of a fluorescence donor and a fluorescence acceptor. In instances where C1 and C2 are a fluorescence donor and acceptor pair and the compound is used in a method that measures a change of fluorescence upon cleavage of the compound, it is preferred that C1 and C2 are separated by no more than 10 amino acids in order to guarantee efficient quenching of the fluorescence donor by the fluorescence acceptor. The skilled person is aware that the crucial parameter is the distance between fluorescence donor and fluorescence acceptor. Thus, in instances where the amino acid sequence separating C1 and C2 is folded into a condensed or twisted secondary structure, resulting in a proximity of C1 and C2 that is closer than in the case of a linear linker, an even longer spacer between C1 and C2 may be allowed.

In preferred embodiments, the pair of C1 and C2 is selected from the group consisting of 2-aminobenzoic acid (ABZ)/pNA, ABZ/ANB-$NH_2$, ABZ/DNP, ABZ/EDDNP, EDANS/DABCYL, TAM/DANSYL, ABZ/Tyr (3-$NO_2$), in particular the pair of C1 and C2 is selected from ABZ/pNA and ABZ/ANB-$NH_2$. It is preferable that C1 and C2 are characterized by a molecular weight of less than 500 g/mol, particularly less than 400 g/mol, more particularly less than 300 g/mol, even more particularly between 100 and 200 g/mol.

The pair of C1 and C2 may also be a protein fluorescence donor and acceptor pair selected from the group consisting of BFP/GFP, BFP/CFP, BFP/YFP, BFP/DsRed, CFP/GFP, CFP/YFP, CFP/mVenus, CeFP/YFP, CeFP/mVenus, CeFP/mCitrine, CFP/DsRed, CFP/mCherry, mTurquoise/mVenus, GFP/YFP, GFP/DsRed, GFP/RFP, Clover/mRuby, Cy3/C5, Alexa Fluor® 488/Alexa Fluor® 555, and FITC/TRITC. The skilled person is aware how to select suitable protein fluorescence donor and acceptor pairs based on their emission and absorbance spectra.

In instances where C1 and C2 are a protein fluorescence donor and acceptor pair, it has to be guaranteed that the relatively large size of the proteins does not impede the cleavage of the compound, and that the sequence Thr-Thr-Ala-Arg is accessible for cleavage by a hydrolytic enzyme. This can be attained, e.g. by increasing the lengths of the amino acid sequence comprising the peptide according to SEQ ID NO:1.

In preferred embodiments, the compound is characterized by formula 2:

ABZ-Thr-Thr-Ala-Arg-ANB-$NH_2$ (formula 2).

In preferred embodiments, the compound is characterized by formula 3:

ABZ-Thr-Thr-Ala-Arg-pNA (formula 3).

Upon cleavage of the compounds characterized by formula 2 or 3, free chromophore molecules are released (ANB-$NH_2$ or pNA, respectively). Thus, an increase of absorbance intensity can be detected at 380-430 nm. In addition, cleavage results in spatial separation of a fluorescence donor (ABZ) from a fluorescence acceptor (ANB-$NH_2$ or pNA, respectively). Thus, fluorescence emitted from ABZ is no longer quenched and an increase of fluorescence intensity can be detected at 420 nm.

In a second aspect, the invention provides an in vitro method for detecting protease activity in a subject's body fluid comprising contacting the body fluid with the compound according to the first aspect of the invention and detecting a signal, wherein the body fluid may comprise a hydrolytic enzyme, in particular a protease, derived from pancreatic cancer cells.

In preferred embodiments, the presence of protease activity in the body fluid indicates the presence of pancreatic cancer and the absence of protease activity in the body fluid indicates the absence of pancreatic cancer.

In preferred embodiments, the invention provides a method for the diagnosis of pancreatic cancer.

In preferred embodiments, the body fluid is selected from blood or urine. In preferred embodiments, the body fluid is urine. Surprisingly, the inventors found that the compound according to the first aspect of the invention is capable of detecting hydrolytic enzyme activity in a urine sample. The hydrolytic enzyme activity is significantly increased in subjects diagnosed with pancreatic cancer compared to healthy subjects (FIG. 1, 2).

In preferred embodiments, the subject has an increased risk of developing pancreatic cancer, is suspected of having pancreatic cancer, has had pancreatic cancer, or has pancreatic cancer.

In preferred embodiments, the compound is provided at a concentration of 0.1-10 mg/ml, particularly 0.25-7.5 mg/ml, more particularly 0.5-5 mg/ml, more particularly 0.75-2 mg/ml, even more particularly about 1 mg/ml, in a measurement buffer having neutral or alkaline pH, preferably a pH between 6.8 and 8.5, more preferably physiological pH, and the body fluid sample is added to the compound at a ratio of 1:2 to 1:10, particularly 1:3 to 1:8, more particularly 1:4 to 1:6, even more particularly about 1:5.

In the context of the present specification, the expression "neutral pH" refers to a pH of approximately 7.0. In the context of the present specification, the expression "physiological pH" refers to a pH of approximately 7.4.

In preferred embodiments, detecting the signal comprises measuring absorbance or fluorescence.

In preferred embodiments, detecting the signal comprises measuring absorbance intensity at 300-500 nm, in particular 380-430 nm, preferably for 40-60 min at 25-40° C., in particular at 36-38° C.

In preferred embodiments, an increase in absorbance indicates the presence of hydrolytic enzyme activity.

In a third aspect, the invention provides a kit comprising a compound according to the first aspect of the invention and a measurement buffer.

In a fourth aspect, the invention provides the use of the compound according to the first aspect, the method according to the second aspect or the kit according to the third aspect for the detection of pancreatic cancer, or for monitoring a subject that has an increased risk of developing pancreatic cancer, is suspected of having pancreatic cancer or has had pancreatic cancer.

Depending on what the method of the second aspect is to be used for, the term "subject" may have different limitations. For example, if the method is to be used for detecting pancreatic cancer or screening subjects for pancreatic cancer, the subject is not known to have pancreatic cancer, i.e. it may or may not have pancreatic cancer. In this example, the subject preferably has an increased risk of developing or is suspected to have pancreatic cancer, or has had pancreatic cancer (i.e. has been cured of detectable pancreatic cancer). "Increased risk" means that one or more risk factors for cancer generally or for the pancreatic cancer can be attributed to the subject, preferably as defined by the American Cancer Society for cancer generally or for pancreatic cancer. Examples of risk factors for pancreatic cancer are: tobacco consumption (in particular smoking), heavy alcohol use, obesity, type 2 diabetes, occupation (workplace exposure to certain chemicals used in the dry cleaning and metal working industries), chronic pancreatitis, age of 50 or older (in particular 65 or older), male gender, ethnicity (in particular African American and Caribbean men of African ancestry), family history of pancreatic cancer (in particular in first degree relatives), and having an inherited syndrome or predisposition (such as hereditary breast and ovarian cancer syndrome, caused by mutations in the BRCA1 or BRCA2 genes; hereditary breast cancer, caused by mutations in the PALB2 gene; familial atypical multiple mole melanoma (FAMMM) syndrome, caused by mutations in the p16/CDKN2A gene and associated with skin and eye melanomas; familial pancreatitis, usually caused by mutations in the PRSSI gene; Lynch syndrome, also known as hereditary non-polyposis colorectal cancer (HNPCC), most often caused by a defect in the MLH1 or MSH2 genes; or Peutz-Jeghers syndrome, caused by defects in the STK11 gene).

The pancreatic cancer may be of any subtype and stage as defined above, i.e. the presence or absence of any subtype and/or stage can be detected.

In a preferred embodiment, the presence of a significant amount of protease activity, or of an amount larger than in a control, indicates the presence of pancreatic cancer, and the absence of a significant amount of protease activity, or of an amount equal to or smaller than in a control, indicates the absence of pancreatic cancer.

In a particular embodiment, the method of the second aspect further comprises confirming the detection of pancreatic cancer by using one or more further means for detecting pancreatic cancer. The further means may be a cancer marker (or "biomarker") or a conventional (non-marker) detection means. The cancer marker can for example be a DNA methylation marker, a mutation marker (e.g. SNP), an antigen marker, a protein marker, a miRNA marker, a cancer specific metabolite, or an expression marker. The conventional means can for example be a biopsy (e.g. visual biopsy examination with or without staining methods for example for protein or expression markers), an imaging technique or a physical, e.g. tactile examination. In preferred embodiments, the further means for pancreatic cancer detection is selected from the group consisting of physical examination (swelling of liver or gallbladder, jaundice, i.e. yellowing of skin and white of the eyes), CT scan, MRI, cholangiopancreatography (in particular endoscopic retrograde cholangiopancreatography, magnetic resonance cholangiopancreatography or percutaneous transhepatic cholangiography), angiography (in particular x-ray angiography, CT angiography or MR angiography), abdominal ultrasound, endoscopic ultrasound, PET scan, blood tests (in particular for bilirubin, CA 19-9 or CEA) and biopsy.

The term "is indicative for" or "indicates" as used herein refers to an act of identifying or specifying the thing to be indicated. As will be understood by persons skilled in the art, such assessment normally may not be correct for 100% of the subjects, although it preferably is correct. The term, however, requires that a correct indication can be made for a statistically significant part of the subjects. Whether a part is statistically significant can be determined easily by the person skilled in the art using several well-known statistical evaluation tools, for example, determination of confidence intervals, determination of p values, Student's t-test, Mann-Whitney test, etc. Details are provided in Dowdy and Wearden, Statistics for Research, John Wiley & Sons, New York 1983. The preferred confidence intervals are at least 50%, at least 60%, at least 70%, at least 80%, at least 90%, at least 95%. The p values are preferably 0.05, 0.01, or 0.005.

The phrase "method for detecting the presence or absence" as used herein with regard to pancreatic cancer refers to a determination whether the subject has the cancer or not. As will be understood by persons skilled in the art, such assessment normally may not be correct for 100% of the subjects, although it preferably is correct. The term, however, requires that a correct indication can be made for a statistically significant part of the subjects. For a description of statistical significance and suitable confidence intervals and p values, see above.

The term "diagnosis" as used herein refers to a determination whether a subject does or does not have cancer. A diagnosis by analysis of protease activity as described herein may be supplemented with a further means as described herein to confirm the cancer detected with the analysis of protease activity. As will be understood by persons skilled in the art, the diagnosis normally may not be correct for 100% of the subjects, although it preferably is correct. The term, however, requires that a correct diagnosis can be made for a statistically significant part of the subjects. For a description of statistical significance and suitable confidence intervals and p values, see above.

The phrase "screening a population of subjects" as used herein with regard to the cancer of the specification refers to the use of the method of the first aspect with samples of a population of subjects. Preferably, the subjects have an increased risk for, are suspected of having, or have had the cancer. In particular, one or more of the risk factors recited herein can be attributed to the subjects of the population. In a specific embodiment, the same one or more risk factors can be attributed to all subjects of the population. For example, the population may consist of subjects characterized by heavy alcohol use and/or tobacco consumption. It is to be understood that the term "screening" refers to a diagnosis as described above for subjects of the population, and is preferably confirmed using a further means as described herein. As will be understood by persons skilled in the art, the screening result normally may not be correct for 100% of the subjects, although it preferably is correct. The term, however, requires that a correct screening result can be achieved for a statistically significant part of the subjects. For a description of statistical significance and suitable confidence intervals and p values, see above.

The term "monitoring" as used herein refers to the accompaniment of a diagnosed cancer during a treatment procedure or during a certain period of time, typically during at least 1 week, 2 weeks, 3 weeks, 4 weeks, 1 month, 2 months, 3 months, 4 months, 5 months, 6 months, 1 year, 2 years, 3 years, 5 years, 10 years, or any other period of time. The term "accompaniment" means that states of and, in particular, changes of these states of a cancer may be detected based on the amount of protease activity, particular based on changes in the amount in any type of periodical time segment, determined e.g., daily or 1, 2, 3, 4, 5, 6, 7, 8, 9, 10, 11, 12, 13, 14 or 15 times per month (no more than one determination per day) over the course of the treatment, which may be up to 1, 2, 3, 4, 5, 6, 7, 8, 9, 10, 11, 12, 15 or 24 months. Amounts or changes in the amounts can also be determined at treatment specific events, e.g. before and/or after every treatment cycle or drug/therapy administration. A cycle is the time between one round of treatment until the start of the next round. Cancer treatment is usually not a single treatment, but a course of treatments. A course usually takes between 3 to 6 months, but can be more or less than that. During a course of treatment, there are usually between 4 to 8 cycles of treatment. Usually a cycle of treatment includes a treatment break to allow the body to recover. As will be understood by persons skilled in the art, the result of the monitoring normally may not be correct for 100% of the subjects, although it preferably is correct. The term, however, requires that a correct result of the monitoring can be achieved for a statistically significant part of the subjects. For a description of statistical significance and suitable confidence intervals and p values, see above.

In a fifth aspect, the invention provides the use of the compound according to the first aspect of the invention in a method of treating pancreatic cancer, the method comprising the steps of carrying out a method according to the second aspect of the invention, and treating pancreatic cancer in a subject for which protease activity, in particular increased protease activity, has been detected.

In another aspect, the invention provides a method of treating pancreatic cancer, comprising carrying out a method according to the second aspect of the invention, and treating pancreatic cancer in a subject for which protease activity, in particular increased protease activity, has been detected.

The term "treatment" or "treating" with respect to cancer as used herein refers to a therapeutic treatment, wherein the goal is to reduce progression of cancer. Beneficial or desired clinical results include, but are not limited to, release of symptoms, reduction of the length of the disease, stabilized pathological state (specifically not deteriorated), slowing down of the disease's progression, improving the pathological state and/or remission (both partial and total), preferably detectable. A successful treatment does not necessarily mean cure, but it can also mean a prolonged survival, compared to the expected survival if the treatment is not applied. In a preferred embodiment, the treatment is a first line treatment, i.e. the cancer was not treated previously. Cancer treatment involves a treatment regimen.

The term "treatment regimen" as used herein refers to how the subject is treated in view of the disease and available procedures and medication. Non-limiting examples of cancer treatment regimens are chemotherapy, surgery and/or irradiation or combinations thereof. The early detection of cancer the present invention enables allows in particular for a surgical treatment, especially for a curative resection. In particular, the term "treatment regimen" refers to administering one or more anti-cancer agents or therapies as defined below. The term "anti-cancer agent or therapy" as used herein refers to chemical, physical or biological agents or therapies, or surgery, including combinations thereof, with antiproliferative, antioncogenic and/or carcinostatic properties.

A chemical anti-cancer agent or therapy may be selected from the group consisting of alkylating agents, antimetabolites, plant alkaloids and terpenoids and topoisomerase inhibitors.

Preferably, the alkylating agents are platinum-based compounds. In one embodiment, the platinum-based compounds are selected from the group consisting of cisplatin, oxaliplatin, eptaplatin, lobaplatin, nedaplatin, carboplatin, iproplatin, tetraplatin, lobaplatin, DCP, PLD-147, JMI 18, JM216, JM335, and satraplatin.

A physical anti-cancer agent or therapy may be selected from the group consisting of radiation therapy (e.g. curative radiotherapy, adjuvant radiotherapy, palliative radiotherapy, teleradiotherapy, brachytherapy or metabolic radiotherapy), phototherapy (using, e.g. hematoporphoryn or photofrin II), and hyperthermia.

Surgery may be a curative resection, palliative surgery, preventive surgery or cytoreductive surgery. Typically, it involves an excision, e.g. intracapsular excision, marginal, extensive excision or radical excision as described in Baron and Valin (Rec. Med. Vet, Special Canc. 1990; 11 (166): 999-1007).

A biological anti-cancer agent or therapy may be selected from the group consisting of antibodies (e.g. antibodies stimulating an immune response destroying cancer cells such as retuximab or alemtuzubab, antibodies stimulating an immune response by binding to receptors of immune cells an inhibiting signals that prevent the immune cell to attack "own" cells, such as ipilimumab, antibodies interfering with the action of proteins necessary for tumor growth such as bevacizumab, cetuximab or panitumumab, or antibodies conjugated to a drug, preferably a cell-killing substance like a toxin, chemotherapeutic or radioactive molecule, such as Y-ibritumomab tiuxetan, I-tositumomab or ado-trastuzumab emtansine), cytokines (e.g. interferons or interleukins such as INF-alpha and IL-2), vaccines (e.g. vaccines comprising cancer-associated antigens, such as sipuleucel-T), oncolytic viruses (e.g. naturally oncolytic viruses such as reovirus, Newcastle disease virus or mumps virus, or viruses genetically engineered viruses such as measles virus, adenovirus, vaccinia virus or herpes virus preferentially targeting cells carrying cancer-associated antigens), gene therapy agents (e.g. DNA or RNA replacing an altered tumor suppressor, blocking the expression of an oncogene, improving a subject's immune system, making cancer cells more sensitive to chemotherapy, radiotherapy or other treatments, inducing cellular suicide or conferring an anti-angiogenic effect) and adoptive T cells (e.g. subject-harvested tumor-invading T-cells selected for antitumor activity, or subject-harvested T-cells genetically modified to recognize a cancer-associated antigen).

In one embodiment, the one or more anti-cancer drugs is/are selected from the group consisting of Abiraterone Acetate, ABVD, ABVE, ABVE-PC, AC, AC-T, ADE, Ado-Trastuzumab Emtansine, Afatinib Dimaleate, Aldesleukin, Alemtuzumab, Aminolevulinic Acid, Anastrozole, Aprepitant, Arsenic Trioxide, Asparaginase *Erwinia chrysanthemi*, Axitinib, Azacitidine, BEACOPP, Belinostat, Bendamustine Hydrochloride, BEP, Bevacizumab, Bexarotene, Bicalutamide, Bleomycin, Bortezomib, Bosutinib, Brentuximab Vedotin, Busulfan, Cabazitaxel, Cabozantinib-S-Malate, CAFCapecitabine, CAPOX, Carboplatin, CARBOPLATIN-TAXOL, Carfilzomib, Carmustine, Carmustine Implant, Ceritinib, Cetuximab, Chlorambucil, CHLORAMBUCIL-PREDNISONE, CHOP, Cisplatin, Clofarabine, CMF, COPP, COPP-ABV, Crizotinib, CVP, Cyclophosphamide, Cytarabine, Cytarabine, Liposomal, Dabrafenib, Dacarbazine, Dactinomycin, Dasatinib, Daunorubicin Hydrochloride, Decitabine, Degarelix, Denileukin Diftitox, Denosumab, Dexrazoxane Hydrochloride, Docetaxel, Doxorubicin Hydrochloride, Doxorubicin Hydrochloride Liposome, Eltrombopag Olamine, Enzalutamide, Epirubicin Hydrochloride, EPOCH, Eribulin Mesylate, Erlotinib Hydrochloride, Etoposide Phosphate, Everolimus, Exemestane, FEC, Filgrastim, Fluorouracil, FU-LV, Fulvestrant, Gefitinib, Gemcitabine Fludarabine Phosphate, Hydrochloride, GEMCITABINE-CISPLATIN, GEMCITABINE-OXALIPLATIN, Gemtuzumab Ozogamicin, Glucarpidase, Goserelin Acetate, HPV Bivalent Vaccine, Recombinant HPV Quadrivalent Vaccine, Hyper-CVAD, Ibritumomab Tiuxetan, Ibrutinib, ICE, Idelalisib, Ifosfamide, Imatinib, Mesylate, Imiquimod, Iodine 131 Tositumomab and Tositumomab, Ipilimumab, Irinotecan Hydrochloride, Ixabepilone, Lapatinib Ditosylate, Lenalidomide, Letrozole, Leucovorin Calcium, Leuprolide Acetate, Liposomal Cytarabine, Lomustine, Mechlorethamine Hydrochloride, Megestrol Acetate, Mercaptopurine, Mesna, Methotrexate, Mitomycin C, Mitoxantrone Hydrochloride, MOPP, Nelarabine, Nilotinib, Obinutuzumab, Ofatumumab, Omacetaxine Mepesuccinate, OEPA, OFF, OPPA, Oxaliplatin, Paclitaxel, Paclitaxel Albumin-stabilized Nanoparticle Formulation, PAD, Palifermin, Palonosetron Hydrochloride, Pamidronate Disodium, Panitumumab, Pazopanib Hydrochloride, Pegaspargase, Peginterferon Alfa-2b, Pembrolizumab, Pemetrexed Disodium, Pertuzumab, Plerixafor, Pomalidomide, Ponatinib Hydrochloride, Pralatrexate, Prednisone, Procarbazine Hydrochloride, Radium 223 Dichloride, Raloxifene Hydrochloride, Ramucirumab, Rasburicase, R-CHOP, R-CVP, Recombinant HPV Bivalent Vaccine, Recombinant HPV Quadrivalent Vaccine, Recombinant Interferon Alfa-2b, Regorafenib, Rituximab, Romidepsin, Romiplostim, Ruxolitinib Phosphate, Siltuximab, Sipuleucel-T, Sorafenib Tosylate, STANFORD V, Sunitinib Malate, TAC, Talc, Tamoxifen Citrate, Temozolomide, Temsirolimus, Thalidomide, Topotecan Hydrochloride, Toremifene, Tositumomab and I 131 Iodine Tositumomab, TPF, Trametinib, Trastuzumab, Vandetanib, VAMP, VeIP, Vemurafenib, Vinblastine Sulfate, Vincristine Sulfate, Vincristine Sulfate Liposome, Vinorelbine Tartrate, Vismodegib, Vorinostat, XELOX, Ziv-Aflibercept, and Zoledronic Acid or salts thereof.

In another aspect, the invention provides a method of producing the compound according to the first aspect of the invention.

In preferred embodiments, the compound characterized by the formula ABZ[1]-Thr[2]-Thr[3]-Ala[4]-Arg[5]-ANB-$NH_2$[6], where ABZ is 2-aminobenzoic acid, and ANB-$NH_2$ is an amide of 5-amino-2-nitrobenzoic acid, is produced according to a process performed on a solid support, preferably having the Fmoc group. Before initiating the process, the solid support is prepared: its volume is increased by repeated washing with hydrophobic solvents, preferably dimethylformamide, methylene chloride or N-methylpyrrolidone, and removing the Fmoc protecting group, preferably by washing with a 10-30% solution of piperidine in solvents such as dimethylformamide, methylene chloride or N-methylpyrrolidone. Next, the process is carried out in subsequent stages:

a) Deposition of 5-amino-2-nitrobenzoic acid ANB on the resin is preceded by washing the solid support with a 3-6% solution of N-methylmorpholine (NMM) in DMF, followed by DMF. Next, a solution of ANB in DMF is prepared, to which TBTU, DMAP and finally diisopropylethylamine (DIPEA) are added in the following excess in relation to the polymer deposition: ANB/TBTU/DMAP/DIPEA, 3:3:2:6. The obtained mixture is added to the resin and mixed until homogeneous, then the resin is filtered off under reduced pressure and washed with solvents such as DMF, DCM and isopropanol. Next, the binding of ANB to the resin is continued by using hexafluorophosphate-O-(7-azabenzotriazol-1-yl)-N,N,N',N'-tetramethyluronium (HATU), followed by hexafluorophosphate-O-(benzotriazol-1-yl)-N,N,N',N'-tetramethyluronium (HBTU) in excess, and after finishing, the solid support is washed successively with DMF, DCM and isopropanol, and gently dried, b) Attachment of the amino acid residue to ANB is carried out using the reaction with the amino acid derivative of Fmoc-Arg (Pbf)-OH, at least a five-fold molar excess of the amino acid derivative in relation to the resin is dissolved in anhydrous pyridine and contacted with the resin with deposited ANB. Next, the whole is cooled to a temperature not lower than 20° C. and $POCl_3$ is added in a ratio of 1:1 to the amount of amino acid derivative used, and mixed. The mixing process is carried out at room temperature and then at an elevated temperature; after the reaction is completed, the resin is filtered off under reduced pressure, washed with DMF and MeOH and gently dried; the obtained intermediate compound is subjected to the process of acylation.

c) Acylation of the resulting intermediate compound is carried out using an amino acid derivative, preferably Fmoc-Ala-OH, and then Fmoc-Thr (tBu)-OH followed by Fmoc-Thr (tBu)-OH and finally by Boz-Abz-OH. Acylation is carried out in stages from residue 6 to 1, using diisopropylcarbodiimide as a coupling agent, which is used in excess. At the end of each step, the resin is washed with DMF and (preferably) subjected to the chloranil test, in which the attachment of the amino acid derivative is monitored.

d) Removing the Fmoc protecting group is carried out by washing with a 10-30% piperidine solution in DMF, and subsequent washing with each of the solvents: DMF, isopropanol and methylene chloride.

e) Separation of the peptide from the resin is carried out using the mixture: TFA, phenol, water, and TIPS, while maintaining a ratio of 88:5:5:2 v/v/v/v, respectively; the mixture is stirred for at least one hour, preferably for three hours, and the resulting precipitate is filtered off under reduced pressure, washed with diethyl ether, and the resulting peptide is centrifuged.

f) Preparation of the finished product is carried out by dissolving the peptide in water by means of ultrasound, and lyophilisation.

In preferred embodiments, the compound characterized by the ABZ[1]-Thr[2]-Thr[3]-Ala[4]-Arg[5]-pNA[6] where ABZ is 2-aminobenzoic acid, and pNA is paranitroanilide, is produced according to a process performed on a solid support, preferably having the Fmoc group. Before initiating the process, the solid support is prepared: its volume is increased by repeated washing with hydrophobic solvents, preferably dimethylformamide, methylene chloride or N-methylpyrrolidone, and removing the Fmoc protecting group, preferably by washing with a 10-30% solution of piperidine in solvents such as dimethylformamide, methylene chloride or N-methylpyrrolidone; then the process is carried out in subsequent stages:

a) Attachment of the third amino acid residue (Fmoc-Ala) to the resin is carried out using the appropriate amino acid derivative at a 9-fold molar excess in relation to the resin deposition, which is dissolved in anhydrous methylene chloride. The mixture is then stirred for at least two hours at room temperature; after completing the reaction, the resin is filtered off under reduced pressure and washed with DMF and MeOH, and then dried.

b) In the subsequent steps, attachment of the amino acid residue, hereinafter referred to as acylation, is performed, and the derivative of Fmoc-Thr (tBu)-OH is used, followed by Fmoc-Thr (tBu)-OH and Boc-ABZ-OH; each step is preceded by washing the resin with DMF, for preferably 5 minutes; in subsequent attachments, a coupling agent is used, preferably diisopropylcarbodiimide, which is used in excess. This procedure is repeated twice, and after each step the resin is washed with DMF, and preferably subjected to the chloranil test, in which the attachment of the amino acid derivative is monitored.

c) Removal of the Fmoc protecting group is carried out by washing with a 10-30% piperidine solution in DMF, and subsequent washing with each of the solvents: DMF, isopropanol and methylene chloride.

d) Repeating steps b) to c) until the compound (ABZ[1]-Thr (tBu) 2-Thr (tBu) 3-Ala[4]-OH) is obtained; synthesis is carried out from residue 6 to 3, and then the resulting compound is detached from the solid support using the mixture: TFA:phenol:water:TIPS in the proportions 88:5:5:2, v/v/v/v, respectively, while stirring. After at least two hours, the contents of the flask are filtered off under reduced pressure, and the precipitate is washed with diethyl ether. The precipitate is then centrifuged for preferably 20 minutes, dissolved in water by means of ultrasound, and then lyophilised.

e) Fmoc-Arg (Pbf)-pNA synthesis is carried out in stages; in the first stage, 2 mmol of Fmoc-Arg (Pbf) is dissolved in anhydrous tetrahydrofuran (THF) in the presence of 2 mmol of N-methylmorpholine (NMM), and the carboxyl group of the amino acid derivative is activated with 2 mmol of isobutyl chloride. After 10 minutes of activation, 3 mmol of p-nitroaniline are added, and the reaction is carried out for (preferably) 2 hours at a temperature (preferably) of −15° C., followed by a day at room temperature. When the reaction is completed, the solvent is evaporated and the dry residue is dissolved in ethyl acetate; then the resulting solution is washed successively with saturated aqueous NaCl solution, 10% citric acid, 5% sodium bicarbonate, and dried over anhydrous sodium sulphate; ethyl acetate is distilled under reduced pressure, and the dry residue is dried.

f) Combining the protected peptide ABZ[1]-Thr (tBu) 2-Thr (tBu) 3-Ala[4]-OH with paranitroanilide Arg (Pbf) is based on the following process: the protected peptide $ABZ^1$-Thr (tBu) 2-Thr (tBu) 3-$Ala^4$-OH is dissolved in a small amount of DCM, and then activated with TFFH (tetramethylfluoroformamide) for preferably 30 minutes at a preferable temperature of 0° C., after which a catalytic amount of DMAP and Fmoc-Arg (Pbf) 5-$pNA^6$ is added. The reaction is preferably carried out for 24 hours at room temperature, after which the solvent is evaporated, and the resulting solution is poured with the mixture removing the side protection: TFA:phenol:water:TIPS (88:5:5:2, v/v/v/v), and mixed for preferably 3 hours.

g) The finished product is prepared by dissolving the peptide in water using ultrasound, and then subjecting to lyophilisation.

BRIEF DESCRIPTION OF THE FIGURES

FIG. 1 shows that all samples 1-10 disintegrated, but for samples 3 and 10, the degradation of the ABZ-Thr-Thr-Ala-Arg-ANB-$NH_2$ substrate occurred more efficiently than for materials 2 or 9. This result may be due to the difference in activity and amount of enzymes responsible for proteolysis. In addition, FIG. 1 shows that incubation of a solution of the compound with formula 2 with urine samples from healthy individuals (without a diagnosed cancer) does not lead to an increase in absorbance, and thus no hydrolysis of the test compound occurs. The result indicates the absence of proteolytic enzymes characteristic of pancreatic cancer.

EXAMPLES

Figure 1:
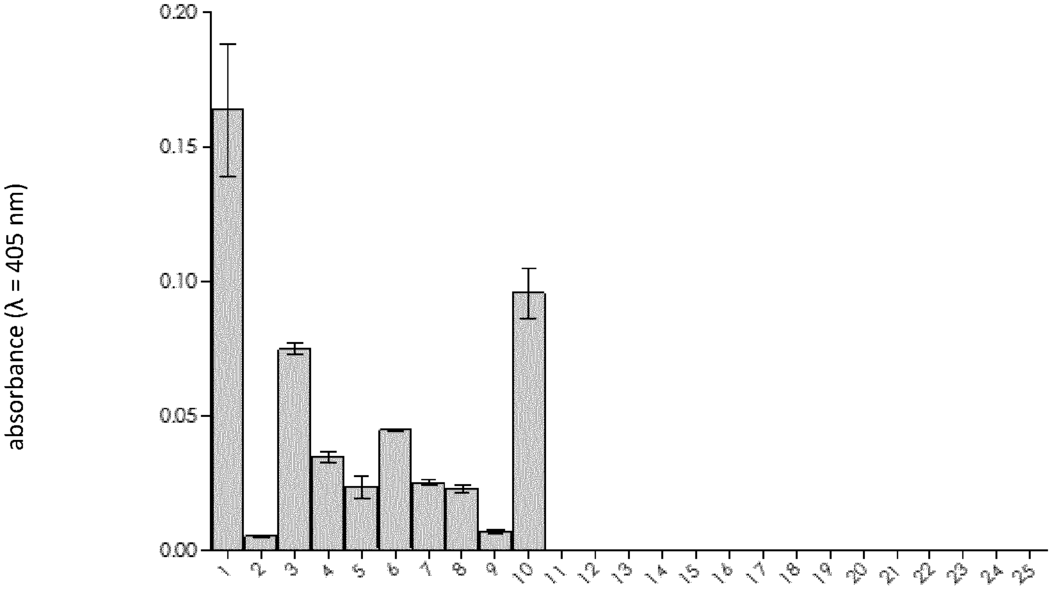
FIG. 1 shows the rate of hydrolysis of substrate (1) ABZ-Thr-Thr-Ala-Arg-ANB-$NH_2$ in urine samples of patients diagnosed with cancer (samples 1-10) and in urine from healthy individuals (11-25). Arabic numbers indicate the number of the selected urine sample.

The invention is illustrated by the following, non-limiting examples of implementation.

Synthesis of compound $ABZ^1$-$Thr^2$-$Thr^3$-$Ala^4$-$Arg^5$-ANB-$NH_2{}^6$ 1. Preparation of the Chromogenic Peptide a) The first stage of the synthesis was to obtain a chromogenic peptide by solid phase synthesis—on a solid support, using Fmoc/tBu chemistry, i.e. using the protection.

A compound with the sequence $ABZ^1$-$Thr^2$-$Thr^3$-$Ala^4$-$Arg^5$-ANB-$NH_2{}^6$, where ABZ is 2-aminobenzoic acid, ANB-$NH_2$ is amide of 5-amino-2-benzoic acid, and ANB is 5-amino-2-benzoic acid, obtained in the process of chemical synthesis in the solid phase using the following amino acid derivatives.

Boc-ABZ, Fmoc-Thr (tBu), Fmoc-Ala, Fmoc-Arg (Pbf), ANB

The synthesis of the compound, i.e. a diagnostic marker for the detection of pancreatic cancer, whose diagnosis is associated with the hydrolysis of this compound under the influence of proteolytic enzymes, was carried out on a solid support enabling the conversion of 5-amino-2-benzoic acid into ANB-$NH_2$ amide:

e.g. amide resin, for instance TentaGel S RAM from RAPP Polymere (Germany), e.g. with a deposit of 0.23 mmol/g.

It is possible to use other commercially available amide resins, including Rink Amide (Germany).

The compound was synthesized manually using a laboratory shaker. For most of the steps, a 25 mL sintered syringe for solid phase synthesis was used as a reactor.

All the obtained final compounds contained ABZ 2-aminobenzoic acid in position 1 of their sequence (i.e. at the N-terminus), and ANB 5-amino-2-nitrobenzoic acid molecule in position 6 (at the C-terminus). ABZ acts as a fluorescence donor, while ANB (5-amino-2-benzoic acid) acts as a fluorescence quencher and chromophore. The peptides contained at least (and preferably) one reactive site in their sequence, located between the amino acid residues Arg-ANB-$NH_2$: at the 5 position of the compound. The synthesis, involving the attachment of amino acid derivatives, is carried out from the residue 6 to 1, i.e. from the C- to N-terminus.

b) Deposition of ANB on TentaGel S RAM resin:

Peptide synthesis was performed on TentaGel S RAM resin (Rapp Polymere) with a deposition of 0.23 mmol/g. In the first stage, the resin was prepared, including its loosening by the wash cycle. Subsequently, the Fmoc amino group protection was removed from the solid support with a 20% solution of piperidine in NMP, and a solvent wash cycle was carried out. To confirm the presence of free amino groups, a chloranil test was performed.

Solvent wash cycle:

DMF 1×10 minutes

IsOH 1×10 minutes

DCM 1×10 minutes

Removal of Fmoc protection:

DMF 1×5 minutes

20% piperidine in NMP 1×3 minutes

20% piperidine in NMP 1×8 minutes

Solvent wash cycle:

DMF 3×2 minutes

IsOH 3×2 minutes

DCM 3×2 minutes c) Chloranil test:

The chloranil test consisted of transferring (using a spatula) several grains of resin from the reactor—a syringe, into a glass ampoule, to which 100 μL saturated solution of p-chloranil in toluene and 50 μL fresh acetaldehyde were added. After 10 minutes, the control of grains colour was carried out.

At this stage, after performing the test, a green grain colour was obtained, which indicated the presence of free amino groups. After confirming the removal of 9-fluorenylmethoxycarbonyl protection from the resin, it was possible to proceed to the next stage, the attachment of the ANB derivative (5-amino-2-nitrobenzoic acid)

d) Deposition of 5-amino-2-nitrobenzoic acid on a solid support

The first step in the synthesis of the peptide library—a mixture of peptides, was ANB deposition on 1 g of resin. Before attaching the chromophore, the resin used for the reaction was washed with the following solvents: DMF, DCM and again DMF, after which the Fmoc protection was removed from the solid support functional group. One cycle of removing Fmoc protection included the following steps:

Removal of Fmoc protection:

20% piperidine in NMP 1×3 minutes

20% piperidine in NMP 1×8 minutes e) Washing

DMF 3×2 minutes

IsOH 3×2 minutes

DCM 3×2 minutes f) Chloranil test for the presence of free amino groups.

The resin with a free amino group was washed with a 5% solution of N-methylmorpholine (NMM) in DMF, followed by DMF. The procedure of removing Fmoc protection and the wash cycle were performed in a Merrifield vessel. In a separate flask, ANB was dissolved in DMF, and TBTU, DMAP, and finally diisopropylethylamine (DIPEA) were subsequently added in the following excess in relation to polymer deposition: ANB/TBTU/DMA/DIPEA, 3:3:2:6. The mixture thus prepared was added to the resin and stirred for 3 hours. The resin was filtered off under reduced pressure, washed with DMF, DCM and isopropanol, and the entire acylation procedure was repeated twice. Hexafluorophosphate-O-(7-azabenzotriazol-1-yl)-N,N,N',N'-tetramethyluronium (HATU), and then hexafluorophosphate-O-(benzotriazol-1-yl)-N,N,N'N'-tetramethyluronium (HBTU) were used to carry out subsequent reactions of ANB attachment to the resin. In the last step, the resin was washed successively with DMF, DCM and isopropanol, and air dried.

g) Attachment of the C-terminal amino acid residue to ANB

The corresponding amino acid derivative (9-fold molar excess relative to resin deposition) was dissolved in pyridine and transferred to the flask containing the resin with ANB deposited. The whole was cooled to −15° C. (ice bath: 1 part by weight $NH_4Cl$, 1 part by weight $NaNO_3$, 1 part by weight ice). After reaching the desired temperature, $POCl_3$ was added (in a 1:1 ratio to the amount of amino acid derivative used) and the whole was stirred on a magnetic stirrer: 20 minutes at −15° C., 30 minutes at room temperature, and 6 hours at 40° C. (oil bath). After completing the reaction, the resin was filtered off under reduced pressure, washed with DMF and MeOH, and left to dry.

In the next step, the residue (alanine) was attached in the P2 position.

Every attachment of amino acid residues was preceded by washing the resin with DMF for 5 minutes. Diisopropylcarbodiimide was used as a coupling agent in subsequent attachments. The procedure was repeated twice.

After each acylation, a resin wash cycle started, followed by the chloranil test to monitor the attachment of the amino acid derivative to the free amino groups of the resin.

Solvent wash cycle:

DMF 3×2 minutes

IsOH 3×2 minutes

DCM 3×2 minutes

Chloranil test:

As a result of the tests, after the first two couplings, the colour of the grains was first green and then grey, so it was necessary to carry out another acylation, as a result of which the grains of the resin tested with the chloranil test were colourless. This indicated the attachment of ANB to TentaGel S RAM resin, which enabled moving to the next stage of peptide synthesis.

h) Attachment of further protected amino acid residues:

The resin together with the attached ANB residue in the reactor was washed with DMF, followed by deprotection of the Fmoc from the amino group to attach the protected amino acid alanine derivative.

Removal of Fmoc protection:

DMF 1×5 minutes

20% piperidine in NMP 1×3 minutes

20% piperidine in NMP 1×8 minutes

Solvent wash cycle:

DMF 3×2 minutes

IsOH 3×2 minutes

DCM 3×2 minutes

Chloranil test:

The chloranil test produced a positive result, as evidenced by the green colour of the resin grains. This enabled moving to the next stage-attachment of the Fmoc-Thr (tBu)-OH amino acid residue.

Attachment of the amino acid derivative:

The process of coupling was preceded by washing the resin in DMF. The composition of the coupling mixture remained unchanged when attaching the protected glutamic acid residue.

At the end of each acylation, a solvent wash cycle was performed according to the given procedure, which was followed by a chloranil test for the presence of free amino groups in the solution.

Solvent wash cycle:

DMF 3×2 minutes

IsOH 3×2 minutes

DCM 3×2 minutes

Chloranil test:

The resin grains during the test carried out after the second acylation were colourless, which enabled moving to the next stage of the synthesis, i.e. the introduction of another protected amino acid derivative-threonine and 2-aminobenzoic acid molecule. The coupling processes followed the procedure discussed earlier.

Tests carried out after attaching the above-mentioned residues showed positive results: the resin grains were colourless.

2. Removal of the Peptide from the Solid Support

After synthesis, the amide of ABZ-Thr-Thr-Ala-Arg-ANB-$NH_2$ peptide was removed from the solid support, along with the simultaneous removal of the side protection with the mixture: TFA:phenol:water:TIPS (88:5:5:2, v/v/v/v) in a round-bottomed flask on a magnetic stirrer.

After 3 hours, the contents of the flask were filtered off under reduced pressure on a sintered (Schott) funnel and washed with diethyl ether. The resulting sediment was centrifuged on a SIGMA 2K30 centrifuge (Laboratory Centrifuges) for 20 minutes. The precipitate obtained after centrifugation is dissolved in water by means of ultrasound and lyophilised.

Identity/characteristics of a new compound-HPLC analysis, MS

HPLC conditions: RP Bio Wide Pore Supelco C8 250 mm 4 mm column, A phase system 0.1% TFA in water, B: 80% acetonitrile in A), flow rate 1 ml/min, UV detection at 226 nm.

Obtaining the compound was confirmed.

Example 2: Preparation of the Compound with the Formula: $ABZ^1$-$Thr^2$-$Thr^3$-$Ala^4$-$Arg^5$-$pNA^6$ The process is carried out in a similar manner to that described in Example 1, except that the corresponding amino acid derivatives and additional substituents are used, and the process is carried out partly in solution and partly on a solid support.

Preparation of p-Nitroanilide Ala a) The first stage of the synthesis was to obtain a protected peptide by solid phase synthesis using Fmoc/tBu chemistry.

$ABZ^1$-Thr (tBu) 2-Thr (tBu) 3-$Ala^4$-OH compound, where ABZ is 2-aminobenzoic acid, was obtained by solid phase chemical synthesis using the following amino acid derivatives:

Boc-ABZ, Fmoc-Thr (tBu), Fmoc-Ala.

The compound was synthesized on a solid support:

2-chloro-chlorotriyl resin, e.g. from Iris BIOTECH GMBH (Germany), with deposition of 1.6 mmol Cl/g groups.

The compound was synthesized manually using a laboratory shaker. Throughout all stages, a 25 ml sintered syringe for solid phase synthesis was used as the reactor.

Peptide synthesis was carried out on a solid support: 2-chloro-chlorotrityl resin, e.g. from Iris BIOTECH GMBH (Germany), with deposition of 1.6 mmol Cl/g groups. In the first stage, the resin was loosened in a wash cycle. Subsequently, the Fmoc amino group protection was removed from the solid support with a 20% solution of piperidine in NMP. Then a solvent wash cycle was carried out. To confirm the presence of free amino groups, a chloranil test was performed.

Solvent wash cycle:

DMF 1×10 minutes

IsOH 1×10 minutes

DCM 1×10 minutes

Removal of Fmoc protection:

DMF 1×5 minutes

20% piperidine in NMP 1×3 minutes

20% piperidine in NMP 1×8 minutes

Solvent wash cycle:

DMF 3×2 minutes

IsOH 3×2 minutes

DCM 3×2 minutes b) Chloranil test:

The chloranil test consisted of transferring (with a spatula) several grains of resin from the reactor—a syringe, into a glass ampoule, and adding 100 μL saturated solution of p-chloranil in toluene and 50 μL fresh acetaldehyde. After 10 minutes, the control of grains colour was carried out.

At this stage, after the test, a green colour of grains was obtained, which indicated the presence of free amino groups. After confirming the removal of the 9-fluorenylmethoxycarbonyl protection from the resin, the attachment of Fmoc-Ala derivative was initiated.

c) Embedding Fmoc-Ala on a solid support

The first step in the synthesis of the peptide library was the deposition of Fmoc-Ala on 1 g of resin. Before attachment of the amino acid derivative, the resin used for the reaction was washed with the following solvents: DMF (dimethylformamide), DCM (methylene chloride) and again with DMF, after which the Fmoc-protection was removed from the solid support functional group. One cycle of Fmoc-protection removal included the following steps:

Removal of Fmoc protection:

20% piperidine in NMP 1×3 minutes

20% piperidine in NMP 1×8 minutes

Washing

DMF 3×2 minutes

IsOH 3×2 minutes

DCM 3×2 minutes

Chloranil test for the presence of free amino groups.

The resin with a free amino group was washed with DMF. In a separate flask, Fmoc-Ala was dissolved in DMF. Next, TBTU, DMAP, and finally diisopropylethylamine (DIPEA) were added in excess to the polymer deposition: Fmoc-Pro/TBTU/DMAP/DIPEA, 3:3:2:6. The obtained mixture was added to the resin and stirred for 3 hours. The resin was filtered off under reduced pressure, washed with DMF, DCM and isopropanol, and the entire acylation procedure was repeated twice. Hexafluorophosphate-O-(7-azabenzotriazol-1-yl)-N,N,N',N'-tetramethyluronium (HATU), followed by hexafluorophosphate-O-(benzotriazol-1-yl)-N, N,N',N'-tetramethyluronium (HBTU) were used to conduct subsequent reactions of Fmoc-Pro attachment to the resin. In the last step, the resin was washed successively with DMF, DCM and isopropanol, and air dried.

c. Attachment of further protected amino acid residues:

The resin together with the attached Fmoc-Ala residue in the reactor was washed with DMF, followed by deprotection of Fmoc from the amino group to attach the protected threonine derivative.

Removal of Fmoc protection:

DMF 1×5 minutes 20% piperidine in NMP 1×3 minutes 20% piperidine in NMP 1×8 minutes Solvent wash cycle:

DMF 3×2 minutes

IsOH 3×2 minutes

DCM 3×2 minutes

Chloranil test:

The chloranil test produced a positive result, as evidenced by the green colour of the resin grains. This enabled moving to the next stage-attachment of the Fmoc-Thr (tBu)-OH amino acid residue.

Attachment of the amino acid derivative:

The process of coupling was preceded by washing the resin in DMF. The composition of the coupling mixture remained unchanged when attaching the protected glutamic acid residue.

At the end of each acylation, a solvent wash cycle was performed according to the given procedure, which was followed by a chloranil test for the presence of free amino groups in solution.

Solvent wash cycle:

DMF 3×2 minutes

IsOH 3×2 minutes

DCM 3×2 minutes

Chloranil test:

The resin grains during the test carried out after the second acylation were colourless, which enabled moving to the next stage of the synthesis, i.e. the introduction of another protected amino acid derivative-threonine and 2-aminobenzoic acid molecule. The coupling processes followed the procedure discussed earlier.

Tests carried out after attaching the above-mentioned residues showed positive results: the resin grains were colourless.

d) Removal of peptide from the solid support while maintaining side group protection After completing the synthesis, the protected ABZ-Thr (tBu)-Th (tBu)-Ala-OH peptide was removed from the solid support, retaining the side protection with the mixture: acetic acid: TFE (trifluoroethanol): DCM (2:2:6, v/v/v) in a round-bottomed flask on a magnetic stirrer.

After 2 hours, the contents of the flask were filtered off under reduced pressure on sintered (Schott) funnels, washing with the astringent mixture. The solution was washed with hexane (1:10 v/v), evaporated under reduced pressure and then lyophilised.

e) Chemical synthesis of paranitroanilide Arg derivatives

The mixed anhydrides method was used to synthesize Fmoc-Arg (Pbf)-pNA. In the first step, 2 mmol of Fmoc-Arg (Pbf) were dissolved in anhydrous tetrahydrofuran (THF) in the presence of 2 mmol of N-methylmorpholine (NMM). The carboxyl group of the amino acid derivative was activated with 2 mmol of isobutyl chloride. After 10 minutes of activation, 3 mmol of p-nitroaniline were added. Reactions were carried out for 2 hours at −15° C., and then for 24 hours at room temperature. After completing the reaction, the solvent evaporated and the dry residue was dissolved in ethyl acetate. The resulting solution was washed successively with saturated aqueous NaCl solution, 10% citric acid, and 5% sodium bicarbonate. The resulting solution was dried over anhydrous sodium sulphate, ethyl acetate was distilled off under reduced pressure, and the dry residue was dried in a vacuum desiccator over $P_2O_5$ and KOH.

f) Coupling of the protected peptide with paranitroanilide Arg (Pbf)

The protected $ABZ^1$-Thr (tBu) 2-Thr (tBu) 3-$Ala^4$-OH peptide was dissolved in a small amount of DCM, and subsequently activated with TFFH (tetramethylfluoroformamide) for 30 minutes at 0° C. Then a catalytic amount of DMAP and Arg (Pbf)-pNA was added. The reaction was carried out for 24 hours at room temperature, after which the solvent evaporated. The resulting solution was poured with the mixture removing the side protection: TFA:phenol:water:TIPS (88:5:5:2, v/v/v/v) and mixed in a round bottom flask on a magnetic stirrer for 3 hours.

After this time, cold diethyl ether was added to the flask, and the resulting precipitate was centrifuged in a high speed centrifuge at 5,000 rpm for 20 minutes. The precipitate obtained after centrifugation was dissolved in water by means of ultrasound and then lyophilised.

Identity/characteristics of a new compound-HPLC analysis, MS

HPLC conditions: RP Bio Wide Pore Supelco C8 250 mm 4 mm column, A phase system 0.1% TFA in water, B: 80% acetonitrile in A), flow rate 1 mL/min, UV detection at 226 nm. Obtaining of the compound was confirmed.

Example 3

The study on the application of new compounds was performed on a group of 10 patients diagnosed with pancreatic cancer. For this purpose, the compound with formula 2: ABZ-Thr-Thr-Ala-Arg-ANB-$NH_2$ or formula 3: ABZ-Thr-Thr-Ala-Arg-pNA was dissolved in dimethyl sulfoxide (at a concentration of 0.5 mg/mL); 50 μL of this solution was mixed with 120 μl buffer (200 mM Tris-HCl, pH 8.0) and 80 μL of urine of a person with pancreatic cancer. The measurement was made in a 96-well plate designed for measuring absorbance, and each sample was analysed in triplicate at 37° C. The duration of the measurement was 60 minutes. During the measurement, the wavelength characteristic of the released chromophore (ANB-$NH_2$ or pNA) was monitored at 405 nm (range 380-430 nm).

As a result of the measurement, the colour of the solution increased over time in all urine samples from patients diagnosed with pancreatic cancer. The observed absorbance increase over time was different for each of the tested samples. A different effect was obtained for 15 samples of healthy people, as none of the 15 urine samples tested had an increase in absorbance in the diagnostic range.

The analysis confirmed the use of the compounds, according to the examples, in the diagnosis of pancreatic cancer. The mechanism of action of the new compound is based on its enzymatic hydrolysis in such a place, which leads to the release of free chromophore molecules, respectively, ANB-$NH_2$-amide of 5-amino-2-nitrobenzoic acid or pNA-paranitroaniline, which shows absorbance at 320-480 nm, especially 380-430 nm.

TABLE 1

| Values depicted in FIG. 1 | | | |
|---|---|---|---|
| 1 | 0.128 | 0.152 | 0.2109 |
| 2 | 0.00532 | 0.00469 | 0.04912 |
| 3 | 0.07457 | 0.07826 | 0.07178 |
| 4 | 0.03727 | 0.03636 | 0.03044 |
| 5 | 0.02734 | 0.01944 | 0.02312 |
| 6 | 0.04416 | 0.04476 | 0.04487 |
| 7 | 0.02666 | 0.02332 | 0.025 |
| 8 | 0.02045 | 0.02486 | 0.02345 |
| 9 | 0.00647 | 0.00797 | 0.00596 |
| 10 | 0.08668 | 0.11456 | 0.08522 |

All other values 11-25 equal 0

TABLE 2

Figure 2:
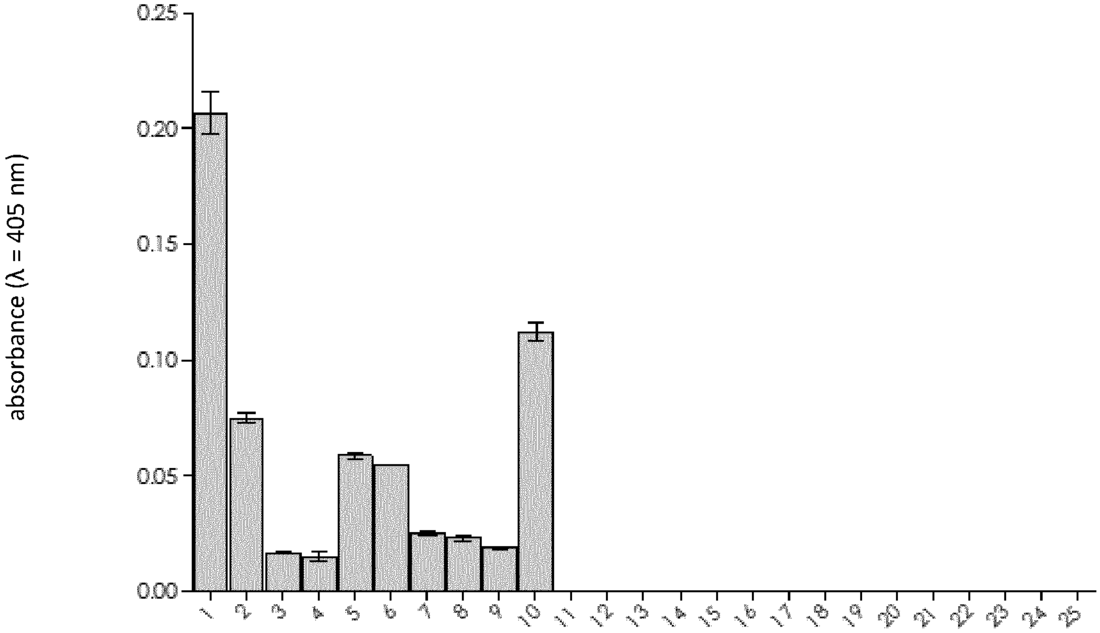
FIG. 2 shows the rate of substrate hydrolysis (2) ABZ-Thr-Thr-Ala-Arg-pNA in urine samples of patients diagnosed with cancer (samples 1-10) and in urine from healthy individuals (11-25). Arabic numbers indicate the number of the selected urine sample. A similar result as described above for FIG. 1 is obtained.

| Values depicted in FIG. 2 | | | |
|---|---|---|---|
| 1 | 0.22 | 0.189 | 0.2109 |
| 2 | 0.07457 | 0.07826 | 0.07178 |
| 3 | 0.01632 | 0.01669 | 0.01723 |

TABLE 2-continued

| Values depicted in FIG. 2 | | |
|---|---|---|
| 4 | 0.01727 | 0.01636 | 0.01044 |
| 5 | 0.05734 | 0.05944 | 0.06152 |
| 6 | 0.05416 | 0.05476 | 0.05487 |
| 7 | 0.02666 | 0.02332 | 0.025 |
| 8 | 0.02045 | 0.02486 | 0.02345 |
| 9 | 0.01947 | 0.01797 | 0.01896 |
| 10 | 0.11668 | 0.11456 | 0.10522 |

All other values 11-25 equal 0

TABLE 3

Figure 3:
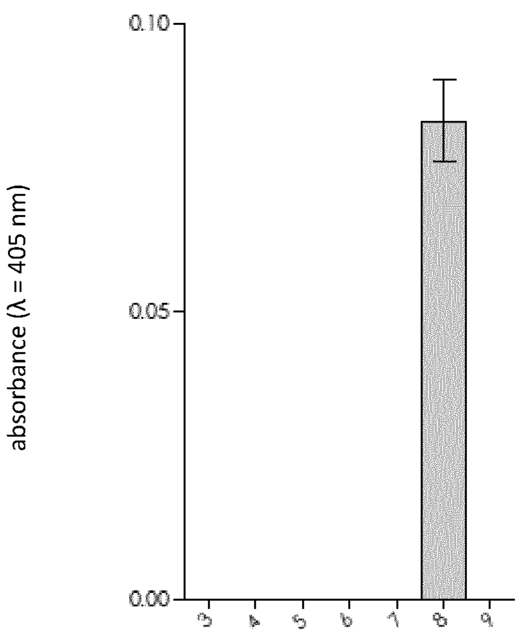
FIG. 3 shows a relationship between the degree of substrate hydrolysis (1) ABZ-Thr-Thr-Ala-Arg-ANB $NH_2$ and the pH environment. Tested pH values are indicated on the x-axis. The relationship between proteolytic activity and pH of reaction environment was assessed. As a result of this experiment, it was found that the tested material had at least one enzyme showing maximum activity at alkaline pH.
Figure 4:
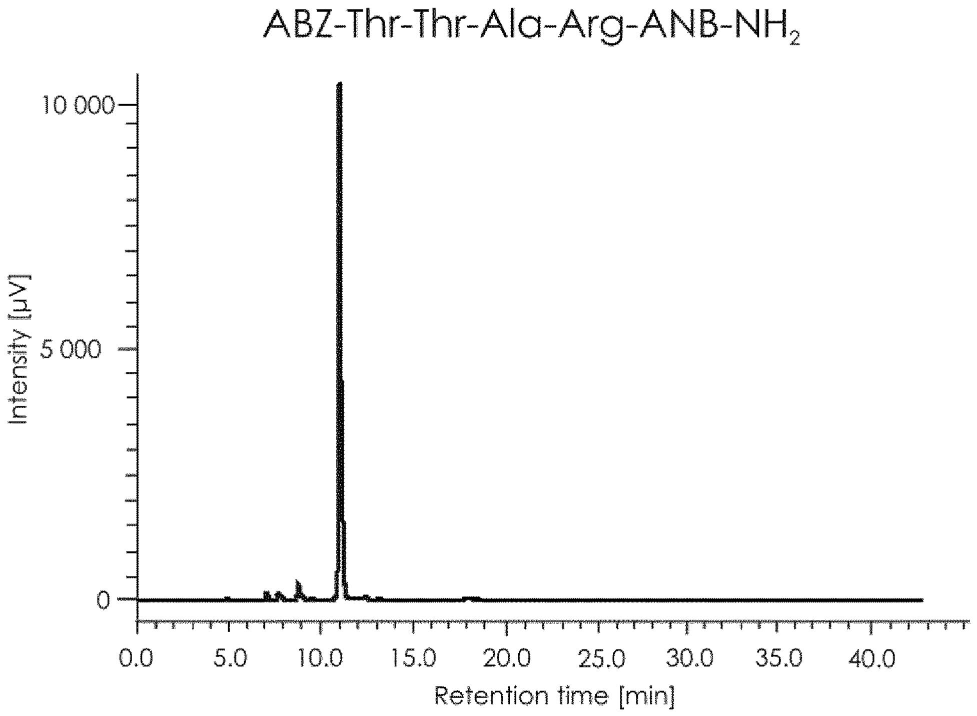
FIG. 4 shows RP HPLC analysis of a randomly selected system containing urine from a person diagnosed with pancreatic cancer. Both compounds (1) (ABZ-Thr-Thr-Ala-Arg-ANB-$NH_2$, shown) and (2) (ABZ-Thr-Thr-Ala-Arg-pNA, not shown) break down into the ABZ-Thr-Thr-Ala-Arg peptide fragment and chromophore (ANB-$NH_2$ or pNA, respectively). A: ABZ-Thr-Thr-Ala-Arg-ANB $NH_2$ substrate in 200 mM Tris-HCl buffer, pH 8.0. B: Hydrolysis of ABZ-Thr-Thr-Ala-Arg-ANB $NH_2$ substrate in urine of patients diagnosed with pancreatic cancer.
Figure 4:
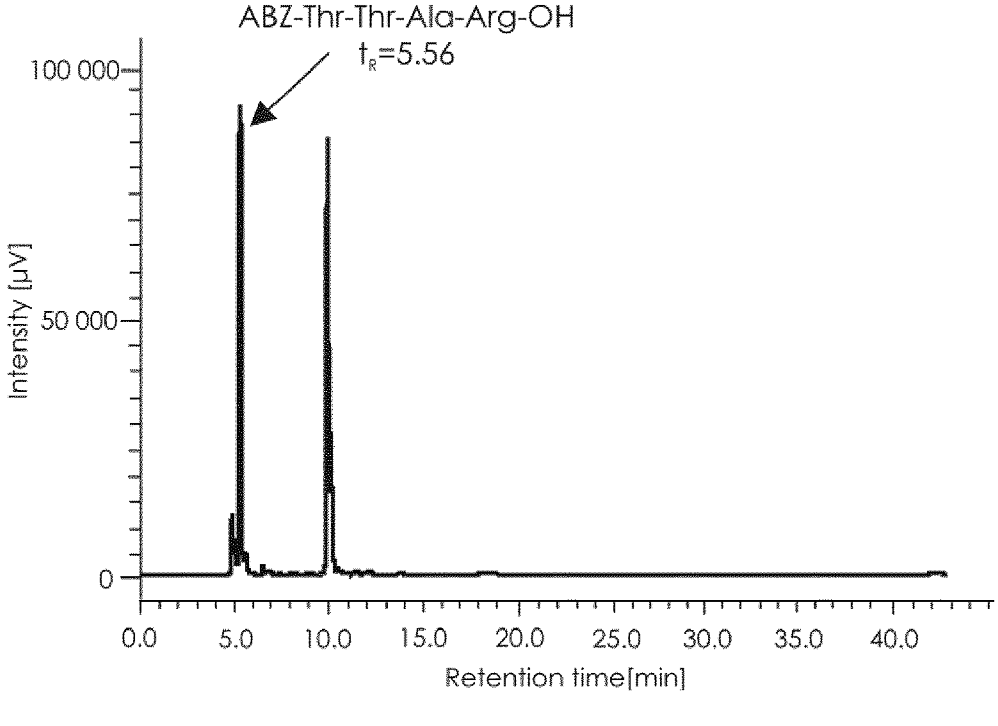

| Values depicted in FIG. 3 | | |
|---|---|---|
| 3 | 0 | 0 | 0 |
| 4 | 0 | 0 | 0 |
| 5 | 0 | 0 | 0 |
| 6 | 0 | 0 | 0 |
| 7 | 0 | 0 | 0 |
| 8 | 0.07661 | 0.07534 | 0.09735 |
| 9 | 0 | 0 | 0 |

The invention claimed is:

1. A compound characterized by formula 1:

X1-Thr-Thr-Ala-Arg-X2      (formula), wherein cleavage of the compound into a fragment 1 comprising X1 and a fragment 2 comprising X2 generates a detectable signal, wherein X1 comprises or consists of a component C1 and X2 comprises or consists of a component C2 and components C1 and C2 are separated by no more than 10 amino acids, wherein the detectable signal is generated upon spatial separation of C1 and C2, by hydrolytic cleaving of the compound, and wherein C1 and C2 are a pair of a fluorescence donor and a fluorescence acceptor.

2. The compound according to claim 1, wherein the sequence Thr-Thr-Ala-Arg is accessible for a hydrolytic enzyme.

3. The compound according to claim 2, wherein the sequence Thr-Thr-Ala-Arg is accessible for a hydrolytic enzyme cleaving the compound into X1-Thr-Thr-Ala-Arg-OH (fragment 1) and NH2-X2 (fragment 2).

4. The compound according to claim 1, wherein one of C1 and C2 is a chromophore having an absorption maximum 1 (AMI) at a wavelength 1, and the compound has an absorption maximum 2 (AM2) at a wavelength 2 that is different from wavelength 1.

5. The compound according to claim 4, wherein C2 is a chromophore having an absorption maximum 1 (AMI) at a wavelength 1, and the compound has an absorption maximum 2 (AM2) at a wavelength 2 that is different from wavelength 1.

6. The compound according to claim 1, wherein the pair of C1 and C2 is selected from the group consisting of 2-aminobenzoic acid (ABZ)/para-nitroaniline (pNA), ABZ/5-amino-2-nitrobenzoic acid (ANB-NH2), ABZ/2,4-dinitrophenyl (DNP), ABZ/ethylene diamine 2,4-dinitrophenyl (EDDNP), 5-((2-aminoethyl)amino) naphthalene-1-sulfonic acid (EDANS)/2-(N, N-dimethyl-4-aminophenyl) azobenzenecarboxylic acid (DABCYL), arboxytetramethylrhodamine (TAM)/5-(dimethylamino) naphthalene-1-sulfonyl (DANSYL), ABZ/Tyr (3-NO2).

7. The compound according to claim 6, wherein the pair of C1 and C2 is selected from ABZ/pNA and ABZ/ANB-NH2.

8. The compound according to claim 1, wherein X2 consists essentially of component C2.

9. The compound according to claim 1, wherein components C1 and C2 are separated by 4 amino acids.

10. A kit comprising a compound according to claim 1 and a measurement buffer.

11. An in vitro method for detecting protease activity in a subject's body fluid, comprising contacting the body fluid with a compound and detecting a signal and wherein the compound is characterized by formula 1:

X1-Thr-Thr-Ala-Arg-X2      (formula), wherein X1 comprises or consists of a component C1 and X2 comprises or consists of a component C2 and components C1 and C2 are separated by no more than 10 amino acids, wherein C1 and C2 are a pair of a fluorescence donor and a fluorescence acceptor, and wherein cleavage of the compound into a fragment 1 comprising X1 and a fragment 2 comprising X2 generates a detectable signal if the body fluid comprises a hydrolytic enzyme derived from pancreatic cancer cells.

12. The in vitro method according to claim 11 for detecting the presence or absence of pancreatic cancer in a subject, wherein the presence of protease activity in the body fluid indicates the presence of pancreatic cancer and the absence of protease activity in the body fluid indicates the absence of pancreatic cancer.

13. The in vitro method according to claim 11 wherein the subject is suspected of having pancreatic cancer, has been assessed to have an increased risk of developing pancreatic cancer, or has had pancreatic cancer.

14. The in vitro method according to claim 11, wherein the body fluid is urine.

15. The method according to claim 11, wherein the compound is provided at a concentration of 0.1-10 mg/mL, in a measurement buffer having neutral or alkaline pH.

16. The in vitro method according to claim 15, wherein the compound is provided at a concentration 0.125-10 mg/ml.

17. The in vitro method according to claim 16, wherein the compound is provided at a concentration 0.25-7.5 mg/ml.

18. The in vitro method according to claim 17, wherein the compound is provided at a concentration 0.5-5 mg/ml.

19. The in vitro method according to claim 18, wherein the compound is provided at a concentration 0.75-2 mg/ml.

20. The in vitro method according to claim 19, wherein the compound is provided at a concentration about 1 mg/ml.

21. The in vitro method according to claim 11, wherein the hydrolytic enzyme is a protease.

22. The method according to 11, wherein detecting the signal comprises measuring absorbance or fluorescence.

23. The method according to claim 22, wherein detecting the signal comprises measuring absorbance intensity at 300-500 nm.

24. The method according to claim 23, wherein detecting the signal comprises measuring absorbance at 380-430 nm.

25. The method according to claim 24, wherein detecting the signal comprises measuring absorbance or fluorescence for 40-60 min at 25-40° C.

26. The method according to claim 25, wherein detecting the signal comprises measuring absorbance or fluorescence at 36-38° C.

27. A method of treating pancreatic cancer, the method comprising the steps of:

(a) carrying out the method according to claim 11, and (b) treating pancreatic cancer in a subject for which protease activity has been detected in step a.

28. A method of treating pancreatic cancer, the method according to claim 27, wherein in step a the protease activity that has been detected is increased protease activity.

* * * * *